US011986593B2

(12) United States Patent
Schaner

(10) Patent No.: US 11,986,593 B2
(45) Date of Patent: May 21, 2024

(54) METHODS AND DEVICES FOR DETERMINING A POSITION OF AN ENDOTRACHEAL TUBE

(71) Applicant: Endolynx, Inc., Jersey City, NJ (US)

(72) Inventor: David Schaner, Jersey City, NJ (US)

(73) Assignee: ENDOLYNX, INC., Jersey City, NJ (US)

(*) Notice: Subject to any disclaimer, the term of this patent is extended or adjusted under 35 U.S.C. 154(b) by 656 days.

(21) Appl. No.: 17/017,620

(22) Filed: Sep. 10, 2020

(65) Prior Publication Data
US 2021/0121651 A1 Apr. 29, 2021

Related U.S. Application Data

(60) Provisional application No. 63/054,520, filed on Jul. 21, 2020, provisional application No. 62/924,862, filed on Oct. 23, 2019.

(51) Int. Cl.
*A61M 16/04* (2006.01)
*A61M 16/00* (2006.01)

(52) U.S. Cl.
CPC .... *A61M 16/0488* (2013.01); *A61M 16/0003* (2014.02); *A61M 16/045* (2014.02);
(Continued)

(58) Field of Classification Search
CPC .... A61M 16/04–0497; A61M 16/0488; A61M 16/0003; A61M 16/024;
(Continued)

(56) References Cited

U.S. PATENT DOCUMENTS 4,134,407 A 1/1979 Elam
6,161,537 A 12/2000 Gravenstein et al.
(Continued)

FOREIGN PATENT DOCUMENTS

WO 2010129327 A1 11/2010
WO 2011068741 A1 6/2011
(Continued)

OTHER PUBLICATIONS

International Preliminary Report on Patentability for Application No. PCT/US20/50266, dated Apr. 26, 2022 (8 pages).
(Continued)

*Primary Examiner* — Joseph D. Boecker
*Assistant Examiner* — Thomas W Greig
(74) *Attorney, Agent, or Firm* — Nutter McClennen & Fish LLP

(57) ABSTRACT

Systems, methods, and devices are disclosed for accurately detecting a position of an endotracheal tube by sensing patient anatomy surrounding the endotracheal tube. Systems of the present disclosure include an endotracheal tube having at least one sensor supported by the endotracheal tube configured to detect surrounding patient anatomy. A signal processing unit can receive data from the sensor and can at least one of (i) identify the detected patient anatomy, for example, vocal cords, (ii) determine a distance between the detected patient anatomy and a known point on the endotracheal tube, and (iii) verify a positioning of the endotracheal tube within a tracheal or esophageal lumen of the patient. In some embodiments, the system can include at least one inflatable component that can extend along an outer surface of the endotracheal tube and support the at least one sensor.

22 Claims, 8 Drawing Sheets

(52) U.S. Cl.
CPC ............. *A61M 2205/3331* (2013.01); *A61M 2205/3375* (2013.01); *A61M 2205/583* (2013.01)

(58) Field of Classification Search
CPC ......... A61M 2205/583; A61M 16/0434–0459; A61B 1/267; A61B 5/065
See application file for complete search history.

(56) References Cited

U.S. PATENT DOCUMENTS

| | | | |
|---|---|---|---|
| 6,322,498 | B1 | 11/2001 | Gravenstein et al. |
| 7,543,586 | B2 | 6/2009 | Qureshi et al. |
| 8,371,303 | B2 | 2/2013 | Schaner et al. |
| 8,905,029 | B2 | 12/2014 | Colburn |
| 9,486,596 | B2 | 11/2016 | Qiu |
| 9,763,624 | B2 * | 9/2017 | Stanislaus ............. A61M 16/04 |
| 10,058,669 | B2 | 8/2018 | Razavi et al. |
| 2005/0148884 | A1 * | 7/2005 | Parks .................... A61B 5/037 |
| | | | 600/488 |
| 2007/0137651 | A1 * | 6/2007 | Glassenberg ..... A61M 16/0415 |
| | | | 128/207.14 |
| 2007/0175482 | A1 | 8/2007 | Kimmel et al. |
| 2010/0006103 | A1 * | 1/2010 | McGinnis ............ A61B 5/1459 |
| | | | 128/207.15 |
| 2010/0261995 | A1 | 10/2010 | McKenna et al. |
| 2010/0317956 | A1 * | 12/2010 | Kartush ............... A61B 5/6859 |
| | | | 600/380 |
| 2011/0030694 | A1 * | 2/2011 | Schaner ............ A61M 16/0459 |
| | | | 128/207.15 |
| 2011/0109458 | A1 | 5/2011 | Shipman |
| 2012/0116156 | A1 | 5/2012 | Lederman |
| 2012/0203101 | A1 | 8/2012 | Prough et al. |
| 2012/0302833 | A1 | 11/2012 | Hayman et al. |
| 2013/0253310 | A1 * | 9/2013 | McKenna ............... A61B 5/742 |
| | | | 600/424 |
| 2013/0281885 | A1 * | 10/2013 | Rowbottom ...... A61M 16/0463 |
| | | | 600/587 |
| 2014/0000622 | A1 * | 1/2014 | Azagury ........... A61M 16/0488 |
| | | | 128/207.15 |
| 2014/0275958 | A1 * | 9/2014 | Victor ................... A61M 16/04 |
| | | | 600/409 |
| 2015/0157819 | A1 * | 6/2015 | Singh ................. A61M 16/0411 |
| | | | 128/200.26 |
| 2015/0209532 | A1 | 7/2015 | Efrati et al. |
| 2016/0038014 | A1 * | 2/2016 | Molnar ..................... A61B 1/05 |
| | | | 128/200.26 |
| 2016/0262603 | A1 * | 9/2016 | Molnar .............. A61B 1/00142 |
| 2017/0189634 | A1 | 7/2017 | Larson |
| 2017/0196478 | A1 * | 7/2017 | Hunter ................ A61B 5/0031 |
| 2017/0232216 | A1 * | 8/2017 | Nave ..................... A61B 1/012 |
| | | | 600/120 |
| 2017/0340216 | A1 | 11/2017 | Morgan et al. |
| 2018/0250484 | A1 | 9/2018 | McCormick et al. |
| 2019/0083728 | A1 * | 3/2019 | Nawn .................. A61B 5/1459 |
| 2020/0113427 | A1 * | 4/2020 | Molnar ................ A61B 90/361 |
| 2021/0121651 | A1 | 4/2021 | Schaner |
| 2022/0105291 | A1 | 4/2022 | Silver et al. |
| 2022/0331556 | A1 | 10/2022 | Baenen et al. |

FOREIGN PATENT DOCUMENTS

| | | | | |
|---|---|---|---|---|
| WO | WO-2011068741 A1 * | 6/2011 | ........... A61B 5/1076 |
| WO | 2013184841 A1 | 12/2013 | |
| WO | WO-2013184841 A1 * | 12/2013 | ........ A61B 5/04884 |

OTHER PUBLICATIONS

International Search Report and Written Opinion for Application No. PCT/US20/50266, dated Jan. 28, 2021 (17 Pages).

Lederman, D., et al, "Automatic endotracheal tube position confirmation system based on image classification—A preliminary assessment", retrieved from the internet at <https://www.sciencedirect.com/science/article/abs/pii/S1350453311000877?via%3Dihub>, Apr. 6, 2011, 6 pages.

Song, Y. et al., "A novel method to position an endotracheal tube at the correct depth using an infrared sensor stylet," retrieved from the internet at <https://link.springer.com/article/10.1007/s12630-013-9898-6>, Feb. 1, 2013, 6 pages.

* cited by examiner

METHODS AND DEVICES FOR DETERMINING A POSITION OF AN ENDOTRACHEAL TUBE

CROSS REFERENCE TO RELATED APPLICATIONS

This application claims the benefit of U.S. Provisional Application No. 62/924,862, filed Oct. 23, 2019 and entitled "Methods and Devices for Determining a Position of an Endotracheal Tube" and U.S. Provisional Application No. 63/054,520, filed Jul. 21, 2020 and entitled "Methods and Devices for Determining a Position of an Endotracheal Tube" each of which is hereby incorporated by reference in its entirety.

FIELD OF THE INVENTION

Illustrative embodiments generally relate to airway management during medical procedures and, more particularly, illustrative embodiments relate to the positioning of an endotracheal tube.

BACKGROUND OF THE INVENTION

Proper positioning of an endotracheal tube (ETT) assists with lung oxygenation and ventilation during medical procedures. A common problem after placement of the ETT is the inability to determine the correct depth at which to secure the ETT. The lumen of an ETT that is positioned too deeply passes beyond the bifurcation of the trachea and the carina, and communicates only with the bronchus of a single lung, referred to as endobronchial intubation. According to the Anesthesiology Society of America's Closed Claims Project, endobronchial intubation accounts for 2% of the adverse respiratory events in adults and 4% in children.

Alternatively, a shallowly positioned ETT may be secured within the lumen in the hypopharynx such that the distal end of the ETT protrudes into the trachea but the airway occlusion cuff (AOC), a circumferential balloon that surrounds the ETT near the distal end of the ETT, is inflated above the vocal cords, creating the illusion of a secured airway that is functionally unsecured. Or the ETT, once positioned correctly in the trachea, may be accidentally pulled too shallowly or migrate upward, causing the ETT to become extubated from the trachea. 121,000 unintended extubations occur in intensive care units (ICUs) in the United States every year, causing 34,000 ventilator associated pneumonias and doubling the length of ICU stays. Lastly, the AOC may be accidentally inflated on the vocal cords, which can cause damage to the vocal cords if left inflated.

SUMMARY OF VARIOUS EMBODIMENTS

In accordance with one embodiment of the invention, an endotracheal system includes an endotracheal tube, at least one sensor supported by the endotracheal tube, and a signal processing unit. The endotracheal tube has a proximal end, a distal end, and a lumen extending between the proximal end and the distal end. The at least one sensor is supported by the endotracheal tube and configured to detect surrounding patient anatomy. The signal processing unit is configured to determine a distance between the detected surrounding patient anatomy and a known point on the endotracheal tube.

In illustrative embodiments, the signal processing unit is further configured to display a visual representation of the distance between the surrounding patient anatomy and the known point on the endotracheal tube. The endotracheal tube may include an inflatable balloon extending longitudinally along an outer surface of the endotracheal tube. The at least one sensor can be positioned on or embedded within the inflatable elongated balloon. In some instances, the elongated balloon is removable with respect to the endotracheal tube.

The endotracheal system can further include an inflatable airway occlusion cuff located closer to the distal end of the endotracheal tube than the proximal end, with the at least one sensor being positioned proximally of the airway occlusion cuff. In some embodiments, the at least one sensor includes a sensor array extending circumferentially around an outer surface of the endotracheal tube and longitudinally along at least a portion of a length of the endotracheal tube with a distal end of the sensor array being proximal of the airway occlusion cuff.

In some embodiments, the at least one sensor is configured to detect at least one of a pressure, capacitance, impedance, acoustics, optoacoustics, ultrasound, and infrared characteristic of the surrounding patient anatomy. The at least one sensor can extend longitudinally along at least a portion of a length of the endotracheal tube. In some embodiments the surrounding patient anatomy includes a larynx. In other embodiments the surrounding patient anatomy includes a vocal cord. The at least one sensor, in some embodiments, is configured to detect a pressure variance of the surrounding patient anatomy exerted at or below a low-pressure threshold.

In accordance with another embodiment of the invention, a method of positioning an endotracheal tube within a trachea of a patient includes inserting an endotracheal tube into a pharynx of the patient, the endotracheal tube having a proximal end, a distal end, and a lumen between the proximal end and the distal end, and moving the endotracheal tube distally such that the distal end of the endotracheal tube is positioned within a tracheal lumen of the patient or an esophageal lumen of the patient. An airway occlusion cuff located towards the distal end of the endotracheal tube is inflated. The method further includes detecting patient anatomy surrounding the endotracheal tube with at least one sensor supported by the endotracheal tube, communicating the data regarding the detected patient anatomy from the at least one sensor to a signal processing unit, and determining a distance between the detected surrounding patient anatomy and a known point on the endotracheal tube.

In illustrative embodiments, the surrounding patient anatomy is at least one vocal cord. The method can further include rotating the endotracheal tube such that an intended anterior side of the endotracheal tube is facing anteriorly, thereby aligning the at least one sensor with the at least one vocal cord. In some such embodiments, aligning the at least one sensor with the at least one vocal cord includes at least one of aligning the at least one sensor such that the at least one sensor comes into direct contact with the at least one vocal cord or orienting the at least one sensor to a known position in relation to the at least one vocal cord. Detecting patient anatomy surrounding the endotracheal tube may further include detecting a presence or absence of a first vocal cord and a second vocal cord.

The method can further include visually representing at least a portion of the endotracheal tube and the detected surrounding patient anatomy on a display. In some embodiments, the endotracheal tube further includes at least one inflatable balloon that extends longitudinally along at least a portion of an outer surface of the endotracheal tube, with the at least one sensor positioned on, or embedded within, the at least one elongate balloon. In some such embodiments, the method further includes aligning the at least one sensor with respect to the surrounding patient anatomy, inflating the at least one elongated balloon such that the at least one sensor moves towards the surrounding patient anatomy, and detecting the surrounding patient anatomy using the at least one sensor while the elongated balloon is inflated.

In accordance with other embodiments of the invention, an endotracheal system includes an elongate tube, an airway occlusion cuff, and a sensor array. The elongate tube has a proximal end, a distal end, and a lumen extending therebetween, and the airway occlusion cuff is located closer to the distal end of the elongate tube than a proximal end of the elongate tube. The sensor array is configured to detect surrounding patient anatomy and extends circumferentially around an outer surface of the elongate tube and extends along a length of the elongate tub proximal to the airway occlusion cuff.

In illustrative embodiments, the sensor array includes a flex circuit extending circumferentially around the outer surface of the elongate tube and an outer case surrounding the flex circuit. In some such embodiments, the flex circuit includes a plurality of infrared emitters and a plurality of phototransistors placed in a circular array around the flex circuit.

In yet another embodiment of the invention, an endotracheal system includes an endotracheal tube having a proximal end, a distal end, and a lumen between the proximal end and the distal end. The system further includes means supported by the endotracheal tube for detecting surrounding patient anatomy and means for determining a distance between the detected surrounding patient anatomy and a known point on the endotracheal tube.

In some embodiments, the means for detecting the distance between the detected surrounding patient anatomy and a known point on the endotracheal tube is further configured to display a visual representation of the distance between the surrounding patient anatomy and the known point on the endotracheal tube. The means supported by the endotracheal tube for detecting surrounding patient anatomy can detect the vocal cord of a patient.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

Illustrative embodiments provide for effective and accurate placement of an endotracheal tube (ETT) within a patient's airway. Various embodiments provide fast, accurate, frequent, and, in some embodiments, continuous, and reliable ETT depth location data of the ETT within the airway. To that end, an endotracheal tube supports at least one sensor that detects patient anatomy surrounding the endotracheal tube when the endotracheal tube is located within an air way of a patient. For example, the sensors can detect one or more characteristic of the surrounding anatomy and transmit the sensed information to a signal processing unit in real-time or near real-time. The signal processing unit then determines the distance between the detected surrounding patient anatomy and a known point on the endotracheal tube.

Moreover, the signal processing unit can create a visualization of the endotracheal tube placement relative to the detected patient anatomy. The anatomy detecting sensors can be positioned on a surface of the endotracheal tube and/or integrated within the endotracheal tube, e.g., integrated within a wall of the endotracheal tube. Additionally, or alternatively, some embodiments of the endotracheal tube can include one or more elongated balloon extending longitudinally along an outer surface of the tube, with the at least one sensor placed on or integrated within the balloon. Systems, methods, and devices of the present disclosure can enable proper placement of an ETT and, in turn, reduce the risk of unintended extubation which can decrease the length of time a patient requires ventilation and reduce the number of times that a practitioner needs to readjust the ETT within the patient's airway. Details of illustrative embodiments are discussed below.

Certain exemplary embodiments are described to provide an overall understanding of the principles of the structure, function, manufacture, and use of the devices, systems, and methods. One or more examples of these embodiments are illustrated in the accompanying drawings. The devices, systems, and methods specifically described and illustrated in the accompanying drawings are non-limiting embodiments. The features illustrated or described in connection with one embodiment may be combined with the features of other embodiments. Such modifications and variations are intended to be included within the scope of the present disclosure.

Figure 1:
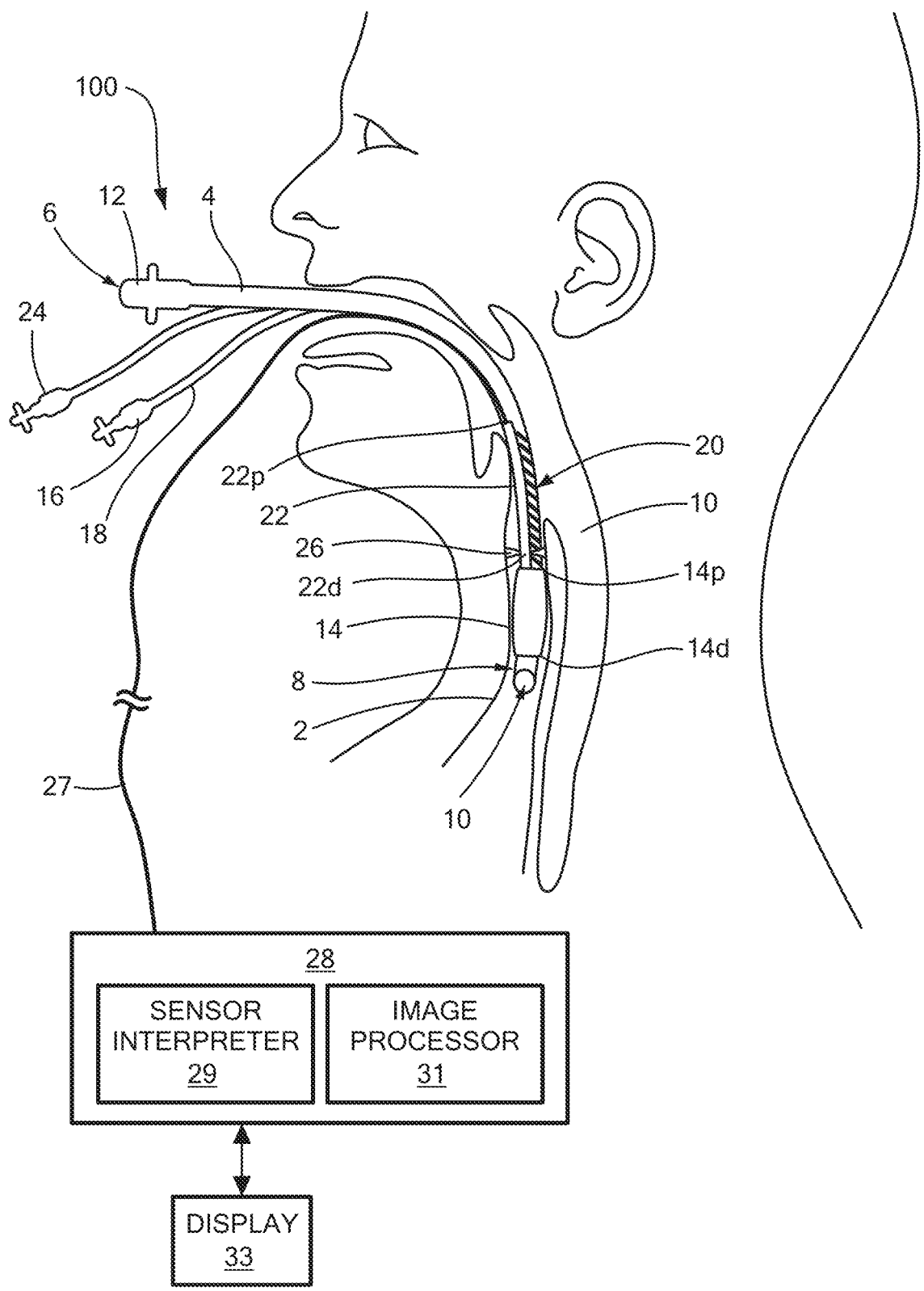
FIG. 1 schematically illustrates one embodiment of an endotracheal tube system in accordance with present disclosure.

FIG. 1 schematically shows one embodiment of an endotracheal system 100 positioned within a trachea 2 of a patient. The system 100 includes an endotracheal tube (ETT) 4 having a proximal end 6 and a distal end 8, with a lumen 10 extending from the proximal end to the distal end of the tube. The endotracheal tube 4 is inserted through a patient's mouth for positioning of the distal end 8 of the endotracheal tube 4 within the patient's trachea 2. The proximal end 6 of the endotracheal tube 4 remains external to the patient. As used herein and shown in FIG. 1, "proximal" is used to refer to a direction towards the end of the ETT 4 that extends externally from the patient upon insertion of the ETT into the patient's airway while the term "distal" is used to refer to the opposite direction. In terms of placement within the trachea 2, proximal refers to closer to a patient's mouth while distal refers to closer to a patient's lungs.

The ETT 4 can include a tube of variable size, diameter, and/or curvature with a plastic connector 12 on the proximal end 6 of the tube 4. The plastic connector 12 can be connected to a bag-valve mask or a ventilator (not shown). In this manner, ETTs of various embodiments can maintain compatibility and usability with existing ventilation systems. With the endotracheal tube 4 positioned within the patient's trachea, the endotracheal tube 4 establishes and maintains an airway of the patient to ensure an adequate exchange of oxygen and carbon dioxide during a surgical procedure. The endotracheal tube 4 has one or more inflatable cuffs 14, also referred to as an airway occlusion cuff (AOC). When inflated, the AOC 14 can seal the trachea 2 and lungs against air leakage, forming a closed, pressurized system and ensuring exchange of oxygen and carbon dioxide between a ventilator and the lungs. When the AOC 14 is inflated while located in the trachea 2 below, or distal to, the vocal cords 26, the AOC 14 produces a seal with the tracheal wall to form a closed air system. Accordingly, proper placement of the endotracheal tube 4 within the trachea 2 is necessary to ensure the efficacy of the endotracheal tube.

Generally, the endotracheal tube 4 is positioned into the trachea 2 of the patient. The AOC 14 is then inflated (e.g., using a pilot balloon 16). The AOC 14 may be connected to the pilot balloon 16 through a small diameter tubing 18 that runs along the length of the endotracheal tube 4. The pilot balloon 16 can include a one-way valve to prevent air from escaping the pilot balloon 16. To adjust the position of the AOC 14, practitioners may, in some instances, deflate the AOC 14, reposition it, and re-inflate the AOC 14 (e.g., using the pilot balloon 16). The AOC 14 extends from a proximal end 14p to a distal end 14d and can be located towards the distal end 8 of the endotracheal tube 4. In some embodiments, the distal end 8 of the endotracheal tube 4 extends distally beyond the distal end 14d of the AOC 14.

The endotracheal tube 4 of various embodiments supports one or more sensors 20 to detect surrounding patient anatomy. By way of non-limiting example, the sensors 20 can detect at least one of a pressure, capacitive, impedance, acoustic, optoacoustic, ultrasound, or infrared characteristic of the surrounding patient anatomy. In the illustrated embodiment of FIG. 1, a sensor cuff 22 supporting the sensors 20 can be affixed to or integrally formed with the endotracheal tube 4. In some embodiments, the sensor cuff 22 can circumscribe the endotracheal tube 4 and extend longitudinally along at least a portion of a length of the tube. The sensor cuff 22 can have a proximal end 22p and a distal end 22d, with the distal end of the sensor cuff located proximally of the AOC 14, i.e., towards the proximal end 6 of the endotracheal tube 4. In some embodiments, the sensor cuff 14 can be inflated using a sensor cuff pilot balloon 24. In this manner, with the endotracheal tube 4 inserted into the patient, the sensor cuff 22 can be inflated such that the sensors 20 are brought closer to, or into contact with, surrounding patient anatomy, such as the vocal cords 26 of the patient. As described in detail below, in other embodiments, one or more sensors supported by the endotracheal tube can be supported by the endotracheal tube 4 in one or more of the following ways:

placed on a surface of one or more elongated balloons,
integrated into one or more elongated balloons,
placed on a surface of the endotracheal tube,
integrated into the endotracheal tube,
placed on a non-inflatable sensor cuff, or
integrated into a non-inflatable sensor cuff.

A signal processing unit 28 receives data from the sensors 20, locates the sensed surrounding patient anatomy, and determines the distance between a known point on the endotracheal tube 4 and the sensed anatomy. For example, the signal processing unit 28 may determine the distance between the distal-most point at the distal end 8 of the endotracheal tube 4 or the proximal-end 114p of the AOC 114 and the detected surrounding patient anatomy, such as the vocal cords 26. To that end, and as discussed in detail below, the signal processing unit 28 can include one or more of a sensor interpreter 29 that determines the location of sensed anatomy and the distance between the sensed anatomy and the known point on the ETT 4 based on sensed data from the sensors 20 of the ETT 4 and an image processor 31 that generates a visual representation of the ETT 4 placement and can communicate with a display 33 to make the visual representation visible to clinicians. While in FIG. 1 the display 33 is illustrated as a separate component in communication with the signal processing unit 28, in some embodiments the display 33 and the signal processing unit 28 can be located within the same component or machine, such as a tablet, computer, etc. Each of these elements can be embodied as hardware (e.g., processors), software and/or firmware. It should be noted that FIG. 1 only schematically shows each of these components and each of these components can be implemented in a variety of conventional manners, such as by using hardware, software, or a combination thereof, across one or more other functional components. For example, the sensor interpreter 29 may be implemented using a plurality of microprocessors executing firmware. As another example, the image processor 31 may be implemented using one or more application specific integrated circuits ("ASICS") and related-software, or a combination of ASICSs, discrete-electronic components (e.g., transistors), and microprocessors. Accordingly, the representation of the signal processing unit 28 and other components in a single box of FIG. 1 is for simplicity purposes only. In fact, in some embodiments, the signal processing unit 28 is distributed across a plurality of different machines, not necessarily within the same housing or chassis.

During use, the sensors 20 detect parameters and/or characteristics of the surrounding patient anatomy. This information is transmitted to the signal processing unit 28, which differentiates between the anatomy surrounding the endotracheal tube 4 and, using that information, determines a location and/or depth of the tube relative to the anatomy. As described in further detail with respect to FIGS. 3 and 4, the signal processing unit 28 generates a visual representation or image of the endotracheal tube 4 placement relative to the detected surrounding patient anatomy. For example, anatomical structures can be defined, mapped, and/or displayed on a screen as recognizable anatomical structures. More particularly, the presence or absence and location of the vocal cords 26 along the length of the endotracheal tube 4 can be determined by using the information sensed by one or more sensor 20.

Detection and identification of the vocal cords 26 by the sensors 20 and signal processing unit 28 can verify that the endotracheal tube is placed within the trachea 2, rather than in the patient's esophagus 10. For example, in some embodiments in which the sensors 20 are infrared sensors, the signal processing unit 28 can receive time-of-flight data, i.e., a measurement of an amount of time for a signal emitted from the sensor 20 to be reflected back to the sensor 20. This can provide distance measurements between the sensor 20 and the surrounding object, i.e., surrounding patient anatomy.

The signal processing unit 28 can use spectroscopic data received from the sensors 20 to identify the unique tissue components of the vocal cords 26 and integrates the time-of-flight data to delineate the vocal cords 26 from surrounding laryngeal structures. The spectroscopic data can be created by sensors 20 using vertical cavity surface emitting lasers (VCSELs) or light emitting diodes (LEDs) as a radiation source and employing time-domain methodology of measuring the time for emitted light to be reflected back to the sensors from surrounding patient anatomy.

The determined location of the vocal cords 26 can then be used as a reference point to calculate the distance from the vocal cords 26 to a known point on the endotracheal tube 4. For example, the known point may be the distal end 8 of the endotracheal tube, the proximal or distal end of the AOC 114, etc., such that determining the distance between the vocal cords 26 and the known point can indicate to the user whether the endotracheal tube 4 is properly positioned relative to the patient anatomy or if adjustment is required. In some embodiments, the sensors 20 can detect surrounding patient anatomy in real-time or near real-time and the signal processing unit 28 can determine the distance between the detected surrounding patient anatomy and the known point on the endotracheal tube, and, in some embodiments, display the visual representation of the same, in real-time or near real-time.

Figure 2:
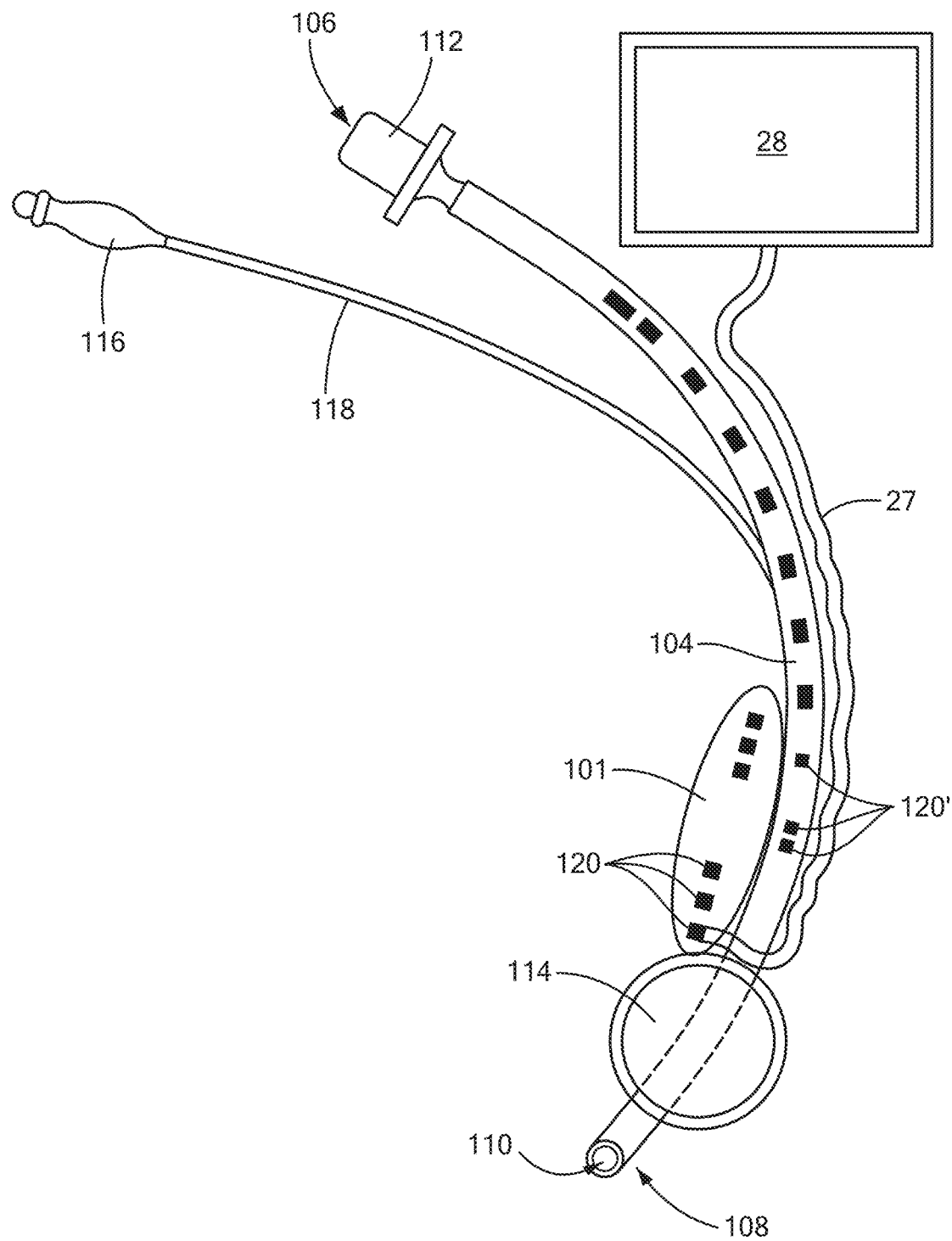
FIG. 2 schematically illustrates another embodiment of an endotracheal tube in accordance with the present disclosure.

FIG. 2 shows another embodiment of an endotracheal tube 104 that can be used in the endotracheal system 100 of FIG. 1. Except as indicated below, the structure, operation, and use of the endotracheal tube 104 is similar or identical to that of the endotracheal tube 4 of FIG. 1, with like-numbered components generally having similar features. Accordingly, description of the structure, operation, and use of such features is omitted for the sake of brevity.

In a manner similar to the endotracheal tube 4 of FIG. 1, this endotracheal tube 104 has a proximal end 106 and a distal end 108 with a lumen 110 extending from the proximal end to the distal end of the endotracheal tube. An airway occlusion cuff 114 can be inflated using a pilot balloon 116 to seal a patient's airway when the endotracheal tube 104 is placed within the trachea 2 of the patient. The endotracheal tube 104 includes an elongated balloon 101 that extends along at least a portion of the length of the endotracheal tube and supports at least one sensor 120 for detecting surrounding patient anatomy. While the illustrated embodiment of FIG. 2 shows a single elongated balloon 101, it will be appreciated that the endotracheal tube 104 can have a plurality of elongated balloons 101 extending along a portion of the length of the tube 104. Additionally, or alternatively, the endotracheal tube 104 can include one or more sensor 120' placed on, or integrated within, the endotracheal tube 104. In some embodiments, the elongated balloon 101 may be omitted. The sensors 120, 120' detect surrounding patient anatomy and communicate with the signal processing unit 28, which determines the distance between the detected patient anatomy and a known point on the endotracheal tube 104, e.g., a distal-most end of the endotracheal tube 104, a point on the elongated balloon 101, etc.

The elongated balloon 101 supports the at least one sensor 120 and assists in determining a proper placement of the endotracheal tube 104 within the trachea 2 of the patient. The elongated balloon 101 can be a linear balloon that extends lengthwise along the outer surface of the endotracheal tube 4 without circumscribing the tube 104. For example, the elongated balloon 101 can be a single linear balloon that can extend along an anterior or a posterior surface of the endotracheal tube 104. In some embodiments that include a plurality of elongated balloons 101, the elongated balloons 101 can be positioned on a plurality of sides of the endotracheal tube 104. Additionally, or alternatively, more than one of the elongated balloons 101 can be positioned on the same side of the endotracheal tube 104 (i.e., elongated balloons 101 can be positioned at different longitudinal locations on the same side of the endotracheal tube 104). In various embodiments, the endotracheal tube 104 can include two bilateral anterior-lateral facing elongated balloons 101. In some embodiments, the elongated balloon 101 can extend over or be incorporated into the AOC 114. The elongated balloon 101 can be a separate component from the AOC 114 and may include a different inflation system (e.g., a separate pilot balloon as show, for example, in FIG. 1 with reference to the sensor cuff pilot balloon 24). Alternatively, in some embodiments, the elongated balloon can be inflated by the pilot balloon 116 and can use the same inflation system as the AOC 114.

In some embodiments, the elongated balloon 101 may be incorporated into the endotracheal tube 104 (e.g., formed as a single piece with the endotracheal tube). In other embodiments, the elongated balloon 101 can be formed as a single piece separate from the endotracheal tube 104. For example, the elongated balloon 101 can be retro-fitted onto an endotracheal tube 104 that is already manufactured. To that end, the elongated balloon 101 may come as part of a sleeve that can be positioned onto the endotracheal tube 104. The sleeve can be sterilizable and re-usable.

In some embodiments, the AOC 114 can also be incorporated as a part of a sleeve that also contains one or more elongated balloon 101. Additionally, sleeves that have one or more AOC 114 and/or elongated balloon 101 may be incorporated over endotracheal tubes 104 that already have at least one AOC.

While the illustrated embodiment of the endotracheal tube 104 has a circular cross-section, a cross-sectional shape of the endotracheal tube 104 can be altered, e.g., to provide a flatter surface contact with patient anatomy, such as the vocal cords 26, when the endotracheal tube 104 is properly oriented. In some embodiments the endotracheal tube 104 has an altered cross-section with a flatter contact surface, which can provide increased sensing ability or better vocal cord contact or interaction between the sensors 120, 120' and the vocal cord 26. For example, an altered cross-section of the endotracheal tube 104 can be a generally triangular shape with the cross section having two longer sides and one shorter side. Rounded points can join the sides of the endotracheal tube with a triangular cross-section to avoid causing trauma to an airway of a patient. With such a configuration, the two longer sides can contact the vocal cords 26 of the patient when the shorter side faces posteriorly. In some embodiments, one or more sensor 120' can be affixed to or integrated into the longer side(s) of the endotracheal tube 104.

As introduced above, the elongated balloon 101 can have one or more sensors 120 to aide in determining proper endotracheal tube 104 placement. The sensors 120 can be integrated into or onto a surface of the elongated balloon 101. It will be appreciated that in various embodiments with a plurality of sensors 120, 120', the plurality of sensors may be positioned on different surfaces. For example, as shown in FIG. 2, the endotracheal tube 104 with the elongated balloon 101 can include one or more sensors 120' located on the surface of the endotracheal tube 104 and one or more sensors 120 located on the surface of the elongated balloon 101.

In some embodiments, the sensor 120 can be a linear sensor and/or the plurality of sensors 120 may be positioned in a linear pattern into or along the surface of the elongated balloon 101. For example, the illustrated embodiment of FIG. 2 includes six sensors 120 positioned linearly along the elongated balloon 101. It will be appreciated that a greater or fewer number of sensors 120 can be used in association with the elongated balloon. Moreover, alternative configuration of sensors 120 are within the scope of the present disclosure. For example, a plurality of sensors 120 can be positioned in a "V" shape configuration on the elongated balloon 101. The elongated balloon 101 can be inflated while the endotracheal tube 104 is positioned within the patient such that the one or more sensors 120 interact with a wall of the trachea 2 or other anatomical structure (e.g., the vocal cords 26) and detect information of the surrounding patient anatomy. In some embodiments, the one or more sensors 120 can contact a wall of the trachea 2 or other anatomical structure, e.g., vocal cords 26, while in other embodiments the one or more sensors 120 can detect information from the trachea 2 or other anatomical structure without direct contact.

The sensors of the various embodiments can be formed from a number of materials. By way of example, material that can change its electrical properties in response to a change in pressure, such as flexible materials or piezoelectric materials, can be used to form the sensors 20, 120, 120'.

The sensor 20, 120, 120' can be electrical, mechanical, electromechanical or optical in nature. In some embodiments, the sensors 20, 120, 120' can employ piezoelectric properties of materials to convert pressure differences into electrical signals. For example, the sensors 20, 120, 120' can detect pressure changes at discrete intervals and convert these pressure changes in to signals. Such conversions may be made, for example, by causing a change in the electrical properties of the sensor 20, 120, 120' by disrupting the transmission of light waves travelling through an optical waveguide. The sensor 20, 120, 120' can capture the change in voltage or current generated in response to a change in pressure at multiple discrete points along the surface of the elongated balloon 101 (e.g., using electrodes) or the surface of the endotracheal tube 104. The electrodes can be passive, generating their own electrical signals, or can require electricity from an outside source that is then modified by the electrodes. For example, these electrical changes can be further modified with the sensor 20, 120, 120' and sent by a wire or series of wires 27 extending from the sensor 20, 120, 120' to the signal processing unit 28. Alternative methods can be used to transmit signals from the sensor 6 to the signal processing unit 8 (e.g., a wireless connection such as RF, WiFi, etc.).

Discussion of the operation, function, and use of the signal processing unit 28 in determining the distance between the known point on the endotracheal tube and detected patient anatomy, and visualization of the same, will now be made with further reference to FIGS. 3 and 4. The signal processing unit 28 can receive and process the signals from each sensor 20, 120, 120'. Additionally, the signal processing unit 28 may be in communication with the display 33, e.g., a computer monitor or a screen of a mobile device. In some embodiments, the display 33 may be located remote of the ETT 104 and the signal processing unit 28 can transmit data to the display through a wired or wireless connection to allow for remote monitoring by a practioner of ETT 104 placement. For example, communication between the signal processing unit 28 and the display 33 may occur over a network, such as a local area network, a wide area network, or the Internet.

Figure 3:
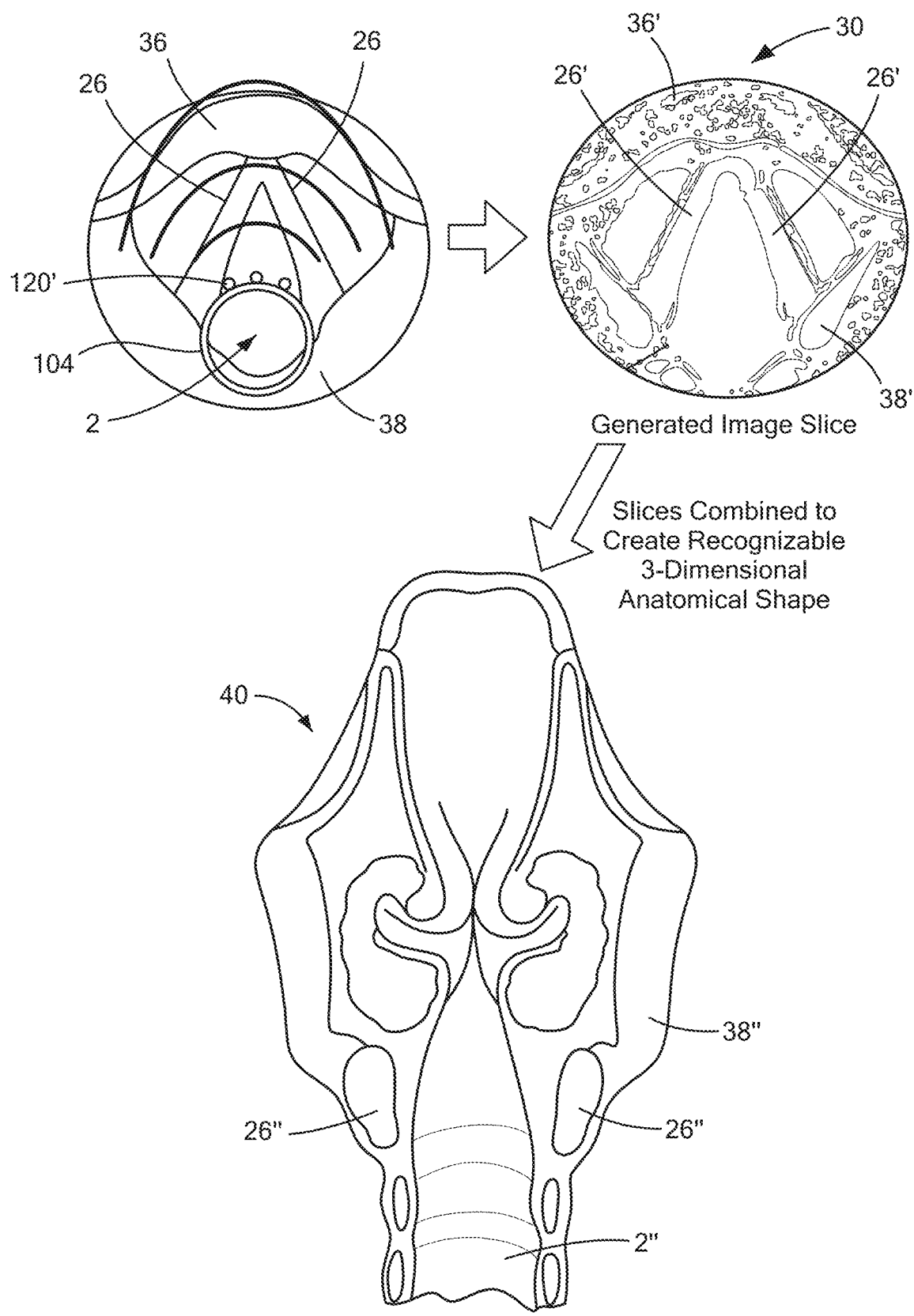
FIG. 3 schematically shows representative imaging of patient anatomy derived from at least one sensor supported by an endotracheal tube in accordance with the present disclosure.

FIG. 3 shows representative embodiments of a sensor map generated by the signal processing unit 28 in accordance with illustrative embodiments. By way of non-limiting example, a sensor map can be a generated image slice 30 and/or a three-dimensional rendering 40 of the patient anatomy sensed by the sensor(s) 20, 120, 120'. A practitioner can use the sensor map 30, 40 to accurately identify and verify the positioning of the endotracheal tube. The sensor maps 30, 40 may be created in a static or dynamic setting when the endotracheal tube 104 is positioned within a lumen of the patient, moved, and/or when one or more elongated balloon 101 is inflated. The sensor maps can be created by quickly triggering the sensors 20, 120, 120' in sequence, or in combinations of sequences, which can prevent sensor to sensor interference.

Based on the signals from the sensor(s) 20, 120, 120' (e.g., pressure data, time-of-flight data, etc.), the signal processing unit 28 can generate an image of the sensed patient anatomy surrounding the sensor(s) 20, 120, 120' and the endotracheal tube 4, 104. For example, using pressure data sensed by the sensor(s) 20, 120, 120', the signal processing unit can generate the image slice 30 to show the vocal cords 26', the epiglottis 36', and/or cartilage 38' surrounding the tracheal lumen 2' into which the endotracheal tube 104 is positioned. The sensor map can be compared with a standardized map of patient anatomy, e.g., of laryngeal, pharyngeal, tracheal, and/or esophageal maps that can be created circumferentially to determine a location of the endotracheal tube 4, 104 in relation to surrounding anatomy.

In some embodiments, the generated image slice 30 can be combined with one or more additional generated image slices based on signal data from one or more additional sensor(s) 20, 120, 120' to create a recognizable three-dimensional rendering 40 of the patient anatomy surrounding the endotracheal tube 4, 104 and sensors 20, 120, 120'. For example, the three-dimensional rendering 40 can include the vocal cords 26", the tracheal lumen 2", and cartilage 38". While not shown in FIG. 3, the three-dimensional rendering 40 can include an accurate representation of a location of the endotracheal tube 4, 104 with respect to the patient anatomy.

Figure 4:
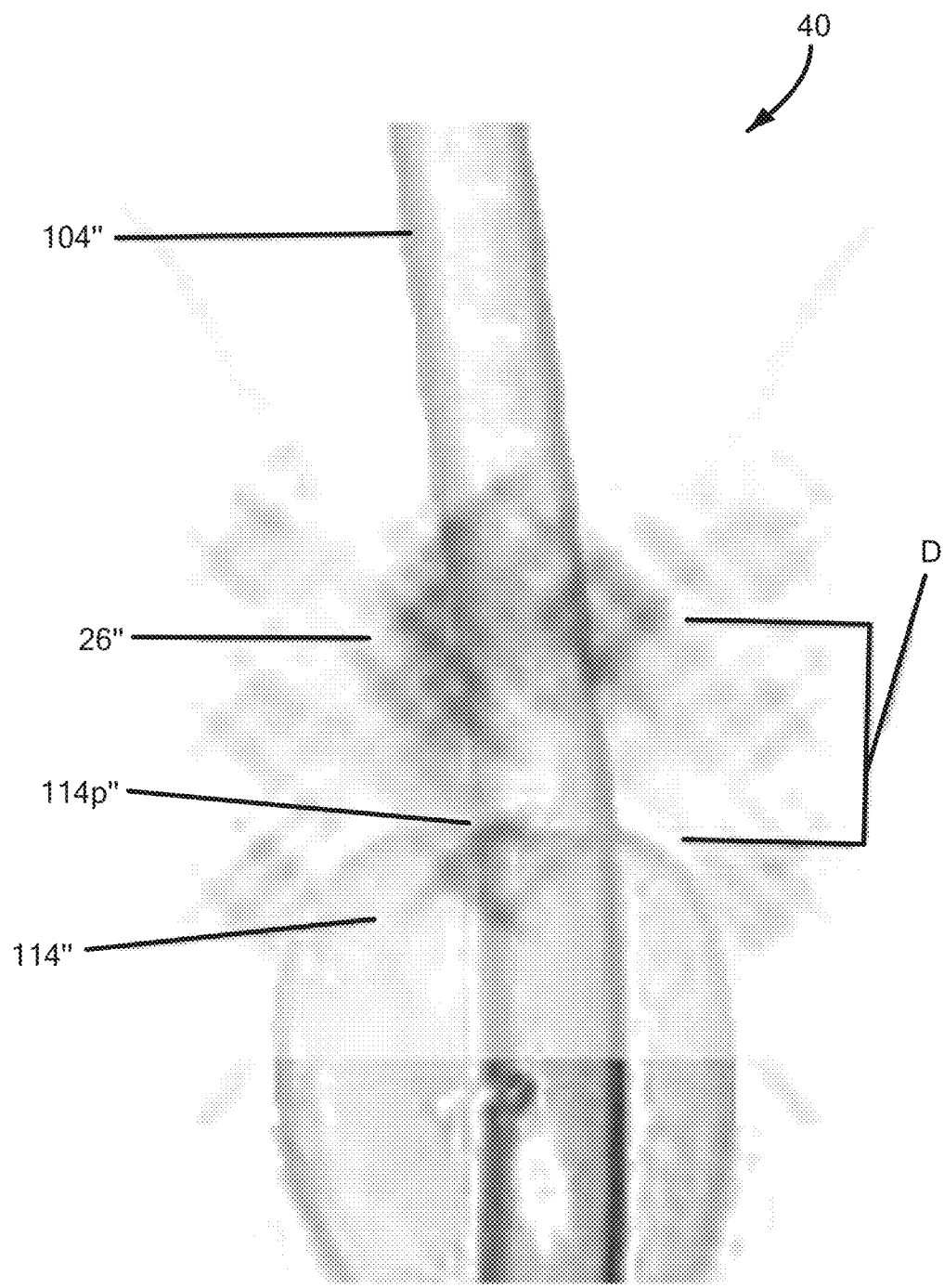
FIG. 4 shows a visual representation of placement of the endotracheal tube of FIG. 2 relative to patient anatomy.

For example, FIG. 4 shows another embodiment of a three-dimensional rendering 140 created by the signal processing device 28, which includes a visual representation of the endotracheal tube 104", including a representation of the AOC 114", and surrounding patient anatomy, e.g., the visual representation of the vocal cords 26". As discussed in detail below, the signal processing unit 28 determines the absolute location of the vocal cords 26 and the distance D between the vocal cords and a known point on the ETT 104, for example the proximal end of the AOC 114p. With the proximal end of the AOC 114p as the known point on the ETT, the distance D represents a critical distance that the ETT can travel proximally, or upwards, within the trachea 2 of the patient before the AOC 114 begins to herniate through the vocal cords 26. This information can assist a practitioner in determining if adjustment of placement of the ETT 104 is required or advisable.

The unique properties of the vocal cords 26 within the larynx allows the vocal cords 26 to be identified by the sensors 120, 120', e.g., infrared sensors and/or pressure sensors, and the signal processing unit 28. In some embodiments, one or more of the sensors 120, 120' can detect pressure characteristics of surrounding patient anatomy. The signal processing unit 28 can amplify and/or filter each signal received from a sensor 120, 120', and transfer each signal or a processed version of the signal to the display 33 where it can be converted into a visualization including color and/or intensity. For example data from the sensors 120, 120' can be transferred to the signal processing unit 28 and converted to show one or more of vocal cords 26 (also referred to as vocal folds), false cords (also referred to as vestibular folds), and/or lumens above, between, and below these cords (also referred to as supraglottic vestibule, the ventricle of the larynx, and the infraglottic lumen respectively). In some instances, the data from the sensors can be transferred to the signal processing unit 28 and converted to show an anterior surface of the esophagus. As will be discussed below, if the sensors 120, 120' detect the presence of the anterior surface of the esophagus, a practitioner can be alerted to an improper placement of the endotracheal tube 104 within the esophagus (as opposed to proper positioning through the larynx and glottis of the patient as intended).

For example, in certain embodiments in which the endotracheal tube 104 includes one or more elongated balloon 101, sensor(s) 120 can be positioned along a length of the elongated balloon 101 such that the sensors 120 extend in a longitudinal direction of the endotracheal tube 104. In this manner, upon inflation of the elongated balloon 101, the sensors 120 can contact surrounding anatomy and can be used to detect pressure, pressure changes, and/or a pressure profile of the surrounding anatomy. The shape of the true vocal cords as well as their stress-strain properties allow the true vocal folds to be identified by the sensors 120, 120' as distinct from other patient anatomy by using, for example, pressure sensing technology (e.g., resistive or capacitive touchscreen sensors) and/or infrared technology. More particularly, the true vocal folds are layered structures, consisting of an inner muscular layer (the thyroarytenoid muscle) with muscle fibers aligned primarily along the anterior-posterior direction, a soft tissue layer of a lamina propria which is ligamentous, and an outmost epithelium layer. The true vocal cords sit directly caudal and medial to the false cords. Each true vocal cord is about 11 mm to about 17 mm long in adult women and about 17 mm to about 25 mm in adult men. Each true vocal cord stretches across the larynx along the anterior-posterior direction, attaching anteriorly to the thyroid cartilage and posteriorly to the anterolateral surface of the arytenoid cartilages. These folds are white in color, due primarily to their ligamentous nature. At rest, the space between these folds is narrowest at the anterior attachment (the anterior commissure) and extends outward in a lateral direction as the coronal plane moves posteriorly, measuring almost the diameter of the larynx at its widest point. These folds are irregularly shaped in the coronal plane, but at the surface closest to the glottis measure approximately 0.5 mm to approximately 1 mm in depth, where the total depth of the vocal fold body measures approximately 1.2 mm to approximately 1.6 mm in depth. The shape and color of these folds, as well as their stress-strain properties, allow them to be identified by pressure sensing and/or infrared sensor (IR) technology. IR sensing technologies in association with various embodiments of the present disclosure will be discussed in further detail below with respect to FIGS. 6-8.

The true cords are stiffer relative to the false cords. Within the true cords themselves, the anterior and posterior portions of the cords are stiffer than the central membranous portion, but the overall stiffness follows a stress-strain curve slope that is relatively low between about 20 kPa to about 50 kPa when a stress of about 0 kPa to about 2.5 kPa is exerted, but quickly rises to a slope of about 200 kPa at about 10 kPa of stress. The curve begins to significantly move upwards at a force of about 2.5 kPa.

In the endotracheal tube system 100 of the present disclosure, one or more sensor 20, 120, 120' can be used to isolate a location of the true vocal cords 26 along its length. The sensor 20, 120, 120' can detect an isolated transverse pressure along a length of about 1 mm to about 1.6 mm that is exerted by each of the true vocal cords as the true vocal cords apply a pressure of about 13 kPa to about 20 kPa. Because no other tissue in the anatomical region above or below the vocal cords has such a stress-strain curve, and because no other tissue results in a signal detectable by a pressure sensor at such a low pressure threshold, the sensor 20, 120, 120' can be used to identify the true vocal cords. In some embodiments, a plurality of sensors 20, 120, 120' can be used to properly identify the symmetrical vocal cords when at least two sensors 20, 120 are expanded outward anterior-laterally by inflation of a component of the ETT 4, 104, e.g., the elongated balloon 101 or the sensor cuff 22. In this manner, the at least two sensors 20, 120 can detect nearly identical signal patterns from the two symmetrical vocal cords consisting of about 1 mm to 1.6 mm indentations at the same longitudinal position along a length of each sensor.

Figure 5:
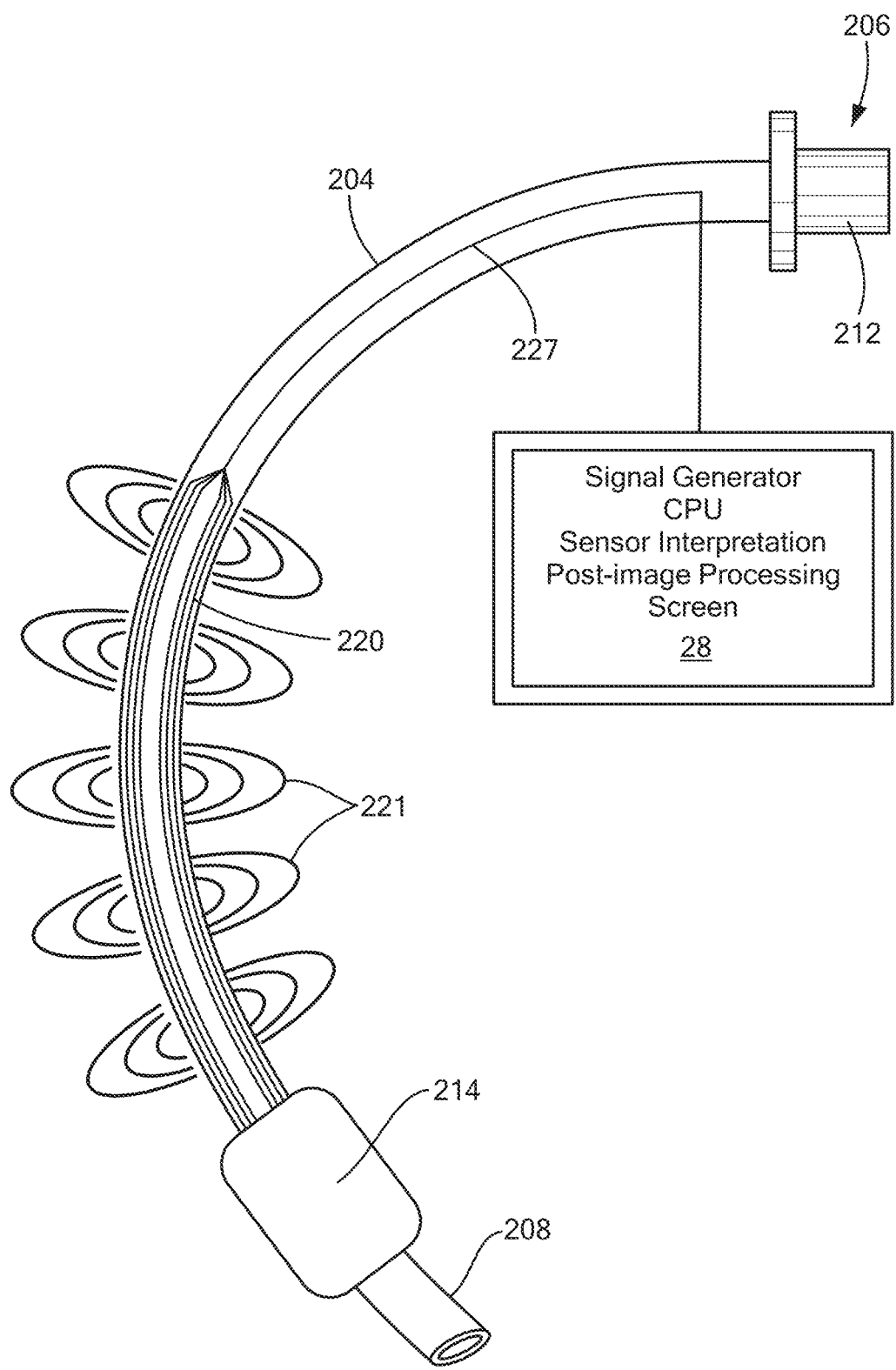
FIG. 5 schematically illustrates another embodiment of an endotracheal tube of the present disclosure.

FIG. 5 schematically illustrates another embodiment of an endotracheal tube 204 in accordance with the present disclosure that can be used in the endotracheal tube system 100 of FIG. 1. Except as indicated below, the structure, operation, and use of the endotracheal tube 204 is similar or identical to that of the endotracheal tube 4 of FIG. 1, with like-numbered components generally having similar features. As shown, the endotracheal tube 204 can have one or more sensors 220 positioned along the length of a surface of the endotracheal tube. By way of non-limiting example, the sensors 220 can include capacitive, impedance, and/or infrared sensors. In some embodiments, the sensors 220 of the endotracheal tube 204 include one or more sensor antennae that extends longitudinally along the endotracheal tube. The sensors 220 can extend proximally along the endotracheal tube 204 from a location of an AOC cuff 214. The AOC cuff 214 can be placed towards a distal end 208 of the endotracheal tube 204.

In some embodiments, one or more of the sensors 220 can be in the form of sensor antennae and need not contact particular anatomy to sense and detect the particular anatomy presence. The sensors 220 can radially emit a sensor signal output 221, which can be communicated to the signal processing unit 28 via a wireless or a wired 227 connection. The sensor signal output 221 can be used, for example, to sense the capacitive, impedance, and/or infrared characteristics of tissue of the larynx and/or esophageal/pharyngeal anatomy at a distance. Different types of tissue have different capacitive, inductive, and impedance characteristics, which can allow these sensors 220 to distinguish one type of tissue from another based on sensed information.

For example, if the endotracheal tube 204 is positioned in the esophagus, the sensors 220 will sense signals that are not similar to signals produced by sensing the presence of other patient anatomy, e.g., the vocal cords 26. More particularly, the anterior surface of the esophagus is a convex non-uniform tissue surface with no prominent features. The sensors 220 sensing this surface (e.g., by pressing against the surface or transmitting signals which contact the surface) would produce a long irregular pattern of signals along a significant length (e.g., greater than about 1 cm) of the sensor 220. Because the anterior surface of the esophagus is concave, the endotracheal tube 204 naturally displaces lateral to the center. Accordingly, bilateral anterior-lateral facing sensors 6 do not sense or display identical patterns. These differences when sensing the vocal cords in comparison to the esophagus can assist with accurately detecting a location of the sensor. Accordingly, because the location of the sensor 220 relative to the endotracheal tube is known, the location of the endotracheal tube 204 with respect to particular patient anatomy may be determined and can be determined, and visualized, by the signal processing unit 28.

Infrared Sensing Embodiments

Figure 6:
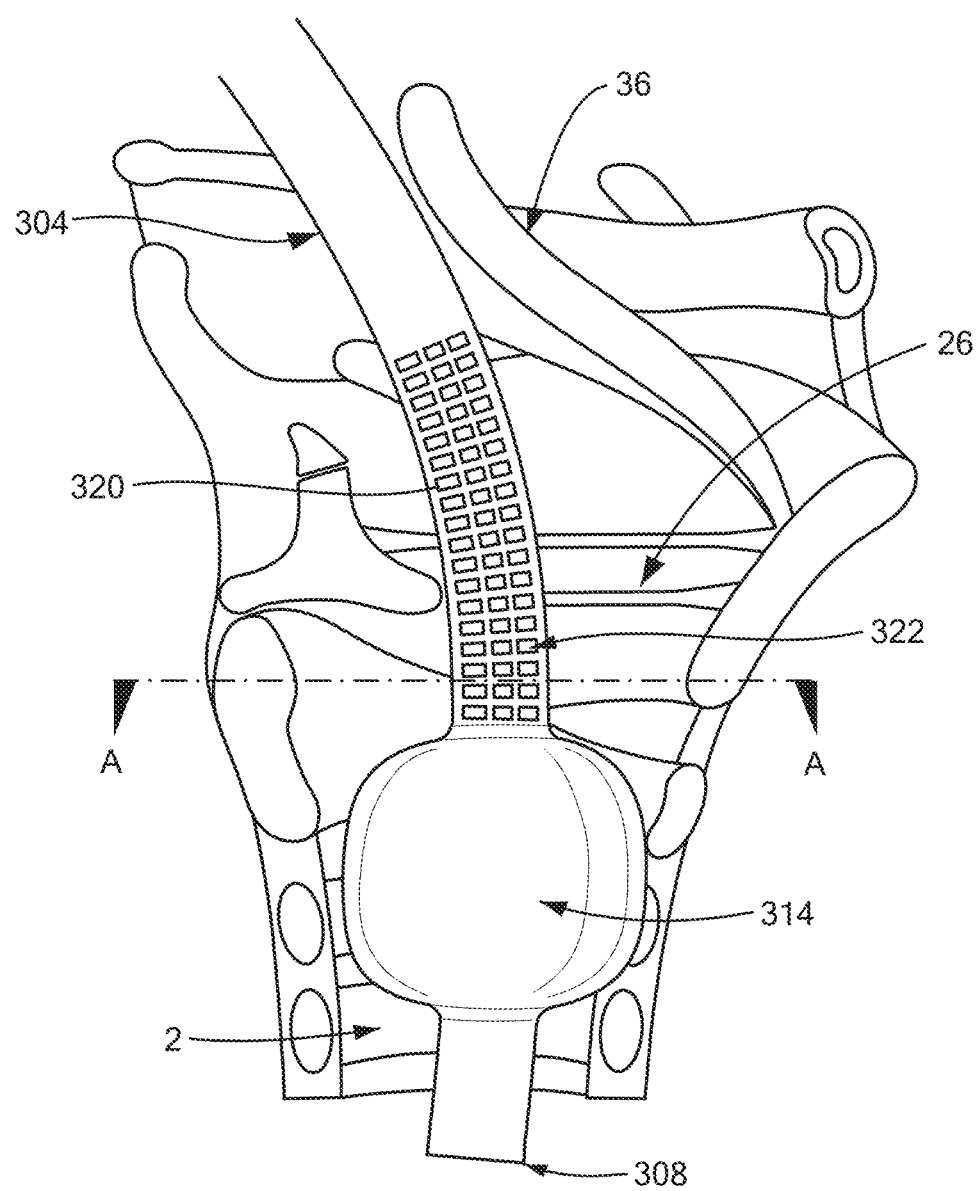
FIG. 6 schematically illustrates another embodiment of an endotracheal tube of the system of FIG. 1 received within a patient airway.
Figure 7:
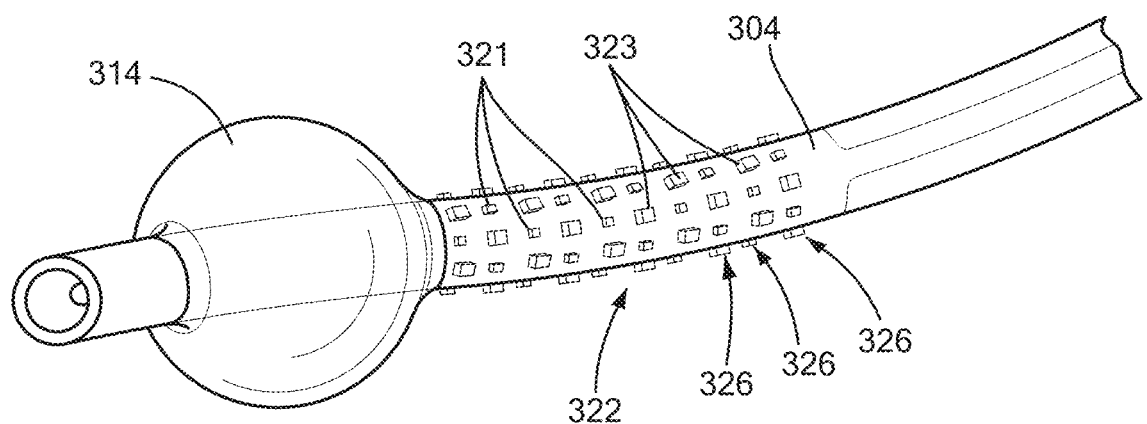
FIG. 7 is a drawing of the endotracheal tube of FIG. 6.
Figure 8:
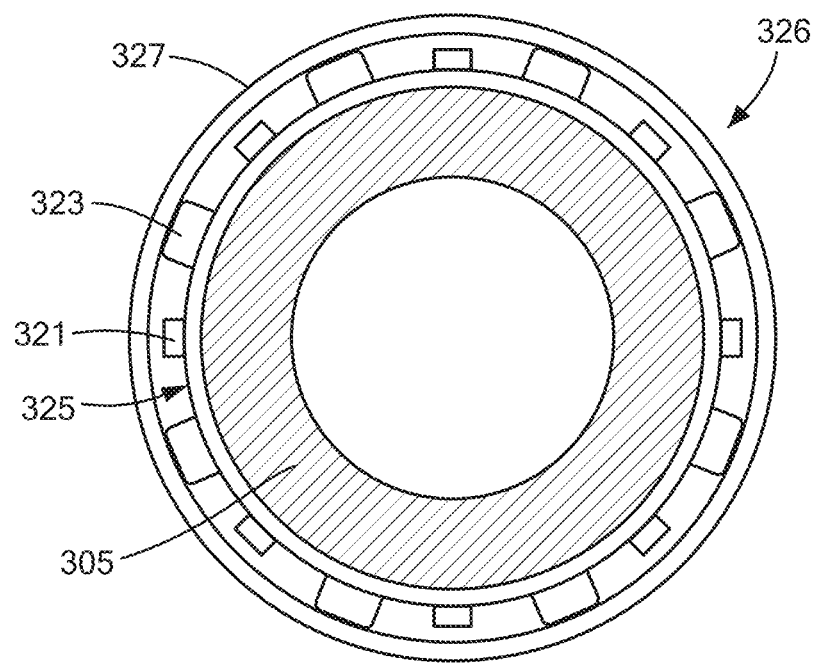
FIG. 8 is a cross-section of the endotracheal tube of FIG. 6 taken along the line A-A.

FIGS. 6, 7, and 8 illustrate another embodiment of an endotracheal tube 304 in accordance with the present disclosure that can be used in the endotracheal tube system 100 of FIG. 1. Except as indicated below, the structure, operation, and use of the endotracheal tube 304 is similar or identical to that of the endotracheal tube 4 of FIG. 1, with like-numbered components generally having similar features. The endotracheal tube 304 includes a plurality of sensors 320. In some embodiments, the plurality of sensors 320 can form a sensor cuff 322 that can extend circumferentially around the endotracheal tube 304. FIG. 6 shows the endotracheal tube 304 positioned within the trachea 2 of a patient and illustrates the positioning of the tube relative to surrounding anatomy, such as the vocal cords 26 and the epiglottis 36. FIG. 7 shows a stand-alone drawing of the endotracheal tube 304 and FIG. 8 shows a cross-sectional view of the endotracheal tube 304 taken along the line A-A of FIG. 6. The endotracheal tube 304 can include an array of infrared (IR) sensors 320, such as LEDs/VCSELs, that can extend circumferentially around the endotracheal tube along a portion of the length of the tube. In this manner, the sensors 320 can continuously determine the position of the ETT 304 within the airway of the patient relative to the vocal cords 26. The IR sensors 320 can be embedded within the endotracheal tube 304

With reference to FIGS. 7 and 8, the sensors 320 can be composed of a series of infrared light emitters 321 and detectors 323 that can be positioned at discrete intervals along the endotracheal tube 304. In some embodiments, the infrared light emitters 321 and detectors 323 can be positioned circumferentially along a length of the endotracheal tube. In one embodiment, an infrared emitter 321 is surrounded at 45-degree angles by four detectors 323 in a repeating pattern at regular intervals to create a grid pattern, which can form a flex circuit 325. For example, in some embodiments, the flex circuit 325 can include a plurality of circular arrays 326, with each circular array extending circumferentially around the endotracheal tube 304. The embodiment illustrated in FIG. 7 shows a flex circuit 325 with 10 circular arrays 326 placed adjacent to one another extending along a length of the endotracheal tube 304. FIG. 8 illustrates a cross-section of one such circular array 326 and includes a pattern of 8 emitters 321 and 8 detectors 323, placed in alternating fashion circumferentially around the endotracheal tube 304. The circular arrays 326 can be placed in alternating alignment along the endotracheal tube 304 such that a grid pattern is formed with the detectors 323 placed adjacent to the emitters 321. In this manner, the sensor cuff 322 can detect circumferential absorbance and reflectance patterns of the patient anatomy surrounding the ETT 304 and can transmit this data to the signal processing unit 28 in the manners described above. The signal processing unit 28 can use the data to determine the absolute location of the vocal cords. Because of the unique anatomical symmetry along an anterior-posterior axis of the trachea at the level of the vocal cords 26, reflectance data collected by the sensors 320 is symmetrical or nearly symmetrical along this axis. Accordingly, the signal processing unit 38, through sequential signal comparison through 180 degrees from a fixed point on the ETT 304, can identify the anterior-posterior axis and match the symmetrical signals to locate the vocal cord level.

An outer case 327 can be molded around the flex circuit 325 to provide encasement and act as a lens. The outer case 327 and the flex circuit 325 can form the sensor cuff 322 which is placed around the tubular body 305 of the endotracheal tube 304. The outer case 327 can be a transparent plastic covering, positioned over the flex circuit 325. This transparent covering allows the infrared energy to transmit from the emitters 321 to the surrounding tissue and allows for the infrared energy to be received from the surrounding tissue by the detectors 323. The sensors 320, i.e., the emitters 321 and detectors 323, can be sequentially initiated to provide localized information for each emitter location. The sensor maps 30, 40, 40' can be created based on the sensed information. The readings from the sensors 320 can distinguish the anatomy and the location of, or absence of, the vocal cords along the length of the endotracheal tube 304.

For example, infrared light can be used to identify the laryngeal anatomy, using time of flight and emissivity/absorptivity technology. Time of flight technology measures the time between discharge of infrared energy and detection of reflected energy and can be used to determine spatial relationships between the object discharging the infrared energy and surrounding anatomical structures. Lumens above and below the vocal cords 26 allow for longer times of flight from emission from the endotracheal tube infrared emitters 321 to detection of the infrared light by the detectors 323 than that of closer adjacent vocal cords. Accordingly, the time of flight data collected by the sensors 320 and transmitted to the signal processing unit 28 provides structure defining information regarding distance of a surrounding structure to a surface of the endotracheal tube 304.

Emissivity/absorptivity measures intensity of reflected thermal radiation and allows characterization of surrounding tissue based on the degree of absorbed or reflected energy. Different tissue types absorb different amounts of infrared energy at specific infrared frequencies. Collagen, for instance, absorbs infrared well at ~1200 nm, whereas water has minimal absorption at the same wavelength. Vocal cord tissue composition is different from tracheal and pharyngeal, and their absorption identities should therefore be definable and localizable.

Methods of Use

Figure 9:
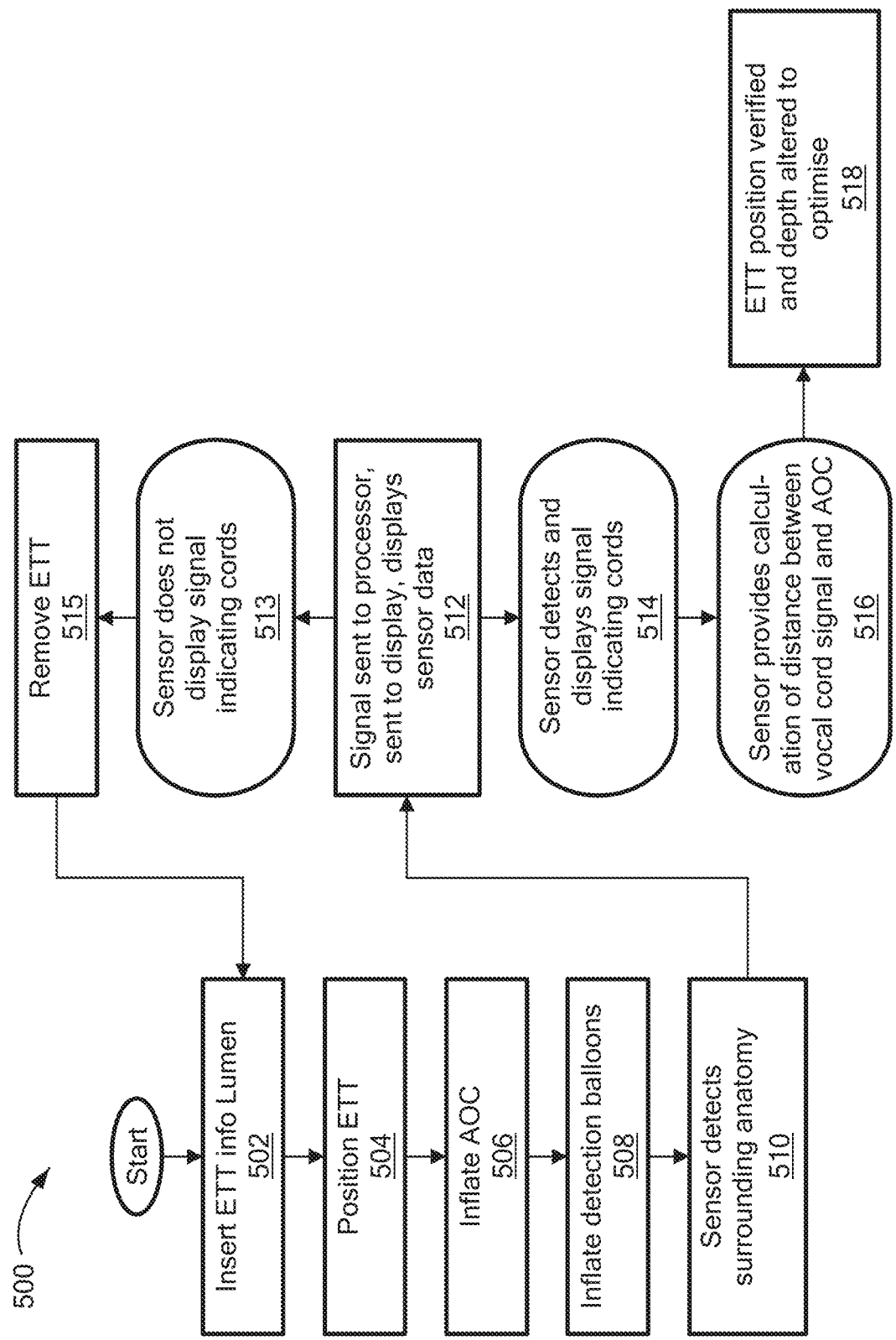
FIG. 9 is a flowchart illustrating one embodiment of a method of determining a position of an endotracheal tube in accordance with the present disclosure.

FIG. 9 shows one embodiment of a process 500 of using an endotracheal tube 4 in accordance with illustrative embodiments of the invention. It should be noted that this process is substantially simplified from a longer process that normally would be used. Accordingly, the process may have many steps that those skilled in the art likely would use. In addition, some of the steps may be performed in a different order than that shown, or at the same time. Those skilled in the art therefore can modify the process as appropriate. The process 500 is described with respect to the embodiment of the endotracheal tube 104 illustrated in FIG. 2. It will be appreciated, however, that the process 500 can be implemented with any of the devices and systems described herein.

The process 500 begins at step 502, which positions the endotracheal tube 104 into a glottis or esophageal lumen of a patient. As described previously, the endotracheal tube 104 can include one or more elongated balloons 101 having one or more sensors 120. Additionally, or alternatively, the endotracheal tube 104 can have one or more sensors 120' positioned along a surface of the endotracheal tube 104. The endotracheal tube 104 can then be rotated within the lumen such that an intended anterior side of the endotracheal tube 104 is facing in an anterior direction (step 504). To that end, a mark can be positioned on the proximal end 106 of the endotracheal tube 104 that is external to the patient to indicate which side of the endotracheal tube 104 is the intended anterior side. The tube 104 is rotated to align one or more sensors 120, 120' to properly detect a presence or absence of the vocal cords. In some embodiments, aligning the sensors 120, 120' can include placing sensors 120 that are located on the elongated balloon 101 such that the sensors can come into direct contact or interact with the vocal cords after the elongated balloon 101 is inflated. Other embodiments align the sensors 120, 120' by placing the sensors 120, 120' such that they can interact with the vocal cords or other surrounding patient anatomy without direct contact, e.g., using infrared sensing technology described above. Aligning the sensors 120, 120' can include placing the sensors in a known position in relation to the vocal cords (e.g., placing the sensors 120, 120' such that they are facing in a direction of a vocal cord).

Next, the AOC 114 can be inflated to occlude the airway of the patient (step 506). Inflating the AOC 114 can include inflating one or more AOCs. In some embodiments where the endotracheal tube 104 includes one or more elongated balloons 101, the balloon 101 can be inflated such that one or more sensors 120 of the elongated balloon 101 contact patient anatomy (step 508). Where a plurality of elongated balloons 101 are used in connection with a single endotracheal tube 104, the plurality of balloons 101 can be fluidically connected such that each of the plurality of balloons 101 can be inflated in a single step. A sensor array or sensor cuff of one or more sensors 120, 120' can contact or interact with surrounding tissue (step 510). For example, sensors 120 on the surface of the balloon 101 can contact the vocal cord 26 or the anterior surface of the esophagus upon inflation of the balloon. In some embodiments, deformation of the vocal cords 26 (or the anterior surface of the esophagus, if the endotracheal tube 104 is positioned within the esophagus) by the inflated elongated balloon(s) 101 allows the sensors 120 to detect the surrounding patient anatomy for the creation of sensor maps. In some embodiments that include one or more sensors 120' located on a surface of the endotracheal tube 104, the sensors 120' and/or sensing signals of the sensors 120, 120' can detect the surrounding patient anatomy (step 510), e.g., using infrared sensing technology described above, without direct contact and/or without requiring inflation of the balloon 101.

The one or more sensors 120, 120' can transmit sensor data to the signal processing unit 28, as discussed above, for further processing (step 512). The signal processing unit 28 can then process the signals from the one or more sensor 120, 120' and convert the data, e.g., a pressure reading, time-of-flight data, etc. into representative image data for visualization on the display 37. For example, the sensor map 30, 40, 40' described above can be generated by the signal processing unit 28. The signal processing unit 28 can send image data to the display 33 such that the sensor data can be displayed as an image to a user in a recognizable manner.

If a sensor detects the presence of vocal cords (step 514) the image on the display screen 33 will show the appropriate and recognizable anatomy, such as vocal cords, false cords, etc. The signal processing unit 28 can include a sensor interpreter that can calculate the distance between the vocal cord signal and the known point, as described above. By way of non-limiting example, the known point can be the AOC 114 or the distal end 108 of the endotracheal tube 104. As discussed above, the distance between the vocal cord 26 (or other recognized patient anatomy) and the known point (e.g., the AOC 114) can be calculated and displayed to the practitioner by the signal processing unit (step 516). The position of the endotracheal tube 104 can be accurately verified using the distance calculation and/or the images of sensed patient anatomy and, if desired, a depth of the endotracheal tube 104 can be adjusted for optimal placement (step 518). For example, a practitioner can ensure that the endotracheal tube 104 is not positioned endobronchially by moving the endotracheal tube 104 proximally within the lumen such that a distance between the AOC 114 and the vocal cords 26 is less than about 1 cm as measured from a distal end of a distal most sensor 120, 120'. Optimal placement of the endotracheal tube 104 can include positioning the endotracheal tube 104 at a depth within the lumen of the trachea 2 to achieve oxygenation and ventilation of both lungs of the patient. In some embodiments, adjusting the depth of the endotracheal tube 104 can include deflating the AOC 114, repositioning the endotracheal tube within the lumen, re-inflating the AOC and repeating some or all of the steps of method 500.

If, in step 512, the image displayed of the patient anatomy sensed by the one or more sensors 120, 120' does not show or indicate the presence of vocal cords 26 (step 513), this can alert the practitioner that the endotracheal tube 104 has been positioned within the lumen of the esophagus rather than the intended lumen of the trachea 2. Accordingly, the endotracheal tube 104 can be removed (step 515) and repositioned into the patient (step 502) with the aim of positioning the endotracheal tube 104 into the lumen of the trachea. The steps of the method 500 can then be repeated to verify a position of the endotracheal tube within the lumen, as discussed above.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. An endotracheal system comprising:
    an endotracheal tube having a proximal end, a distal end, and a lumen between the proximal end and the distal end configured to be positioned in a trachea;
    at least one sensor supported by the endotracheal tube and configured to detect vocal cords(s) and produce sensor data, the at least one sensor comprising at least one infrared emitter and at least one detector; and
    a signal processing unit configured to:
        receive sensor data from the at least one sensor,
        produce data representing the surface of the detected vocal cords(s),
        identify the detected vocal cords(s) when the endotracheal tube is positioned in the trachea, and
        determine a distance between the detected vocal cords(s) and a known point on the endotracheal tube.

2. The endotracheal system of claim 1, wherein the signal processing unit is further configured to display a visual representation of the distance between the detected vocal cords(s) and the known point on the endotracheal tube.

3. The endotracheal system of claim 1, wherein the at least one sensor extends longitudinally along at least a portion of a length of the endotracheal tube.

4. The endotracheal system of claim 1, further comprising:
an inflatable airway occlusion cuff located closer to the distal end of the endotracheal tube than the proximal end; and
wherein the at least one sensor is positioned proximally of the airway occlusion cuff.

5. The endotracheal system of claim 4, wherein the at least one sensor includes a sensor array extending circumferentially around an outer surface of the endotracheal tube and longitudinally along at least a portion of a length of the endotracheal tube with a distal end of the sensor array being proximal of the airway occlusion cuff.

6. The endotracheal system of claim 1, wherein the endotracheal tube further comprises an inflatable elongated balloon extending longitudinally along an outer surface of the endotracheal tube, and
wherein the at least one sensor is positioned on or embedded within the inflatable elongated balloon.

7. The endotracheal system of claim 6, wherein the inflatable elongated balloon is removable with respect to the endotracheal tube.

8. The endotracheal system of claim 1, wherein the detected vocal cords(s) comprise a single vocal cord.

9. The endotracheal system of claim 1, wherein:
the at least one sensor is a first sensor; and
the system further comprises at least one second sensor configured to detect at least one of a pressure, capacitance, impedance, acoustics, optoacoustics, or ultrasound characteristic of the detected vocal cord(s).

10. The endotracheal system of claim 1, wherein the at least one second sensor is configured to detect a pressure variance of the detected vocal cord(s) exerted at or below a low-pressure threshold.

11. A method of positioning an endotracheal tube within a trachea of a patient, the method comprising:
inserting an endotracheal tube into a pharynx of the patient, the endotracheal tube having a proximal end, a distal end, and a lumen between the proximal end and the distal end;
moving the endotracheal tube distally such that the distal end of the endotracheal tube is positioned within a tracheal lumen of the patient or an esophageal lumen of the patient;
inflating an airway occlusion cuff located towards the distal end of the endotracheal tube;
detecting vocal cords(s) surrounding the endotracheal tube with at least one sensor supported by the endotracheal tube when the endotracheal tube is positioned within the tracheal lumen, the at least one sensor comprising at least one infrared emitter and at least one detector;
communicating the data regarding the detected vocal cord(s) from the at least one sensor to a signal processing unit;
producing data representing the surface of the detected vocal cords(s),
identifying, using a signal processor, the detected vocal cords(s), and
determining a distance between the detected vocal cords(s) and a known point on the endotracheal tube.

12. The method of claim 11, wherein the detected vocal cords(s) is one vocal cord.

13. The method of claim 12, further comprising:
rotating the endotracheal tube such that an intended anterior side of the endotracheal tube is facing anteriorly thereby aligning the at least one sensor with the detected vocal cord(s).

14. The method of claim 13, wherein aligning the at least one sensor with the at least one vocal cord includes at least one of:
aligning the at least one sensor such that the at least one sensor comes into direct contact with at the at least one vocal cord; or
orienting the at least one sensor to a known position in relation to the at least one vocal cord.

15. The method of claim 12, wherein detecting vocal cord(s) surrounding the endotracheal tube further comprises detecting a presence or absence of a first vocal cord and a second vocal cord.

16. The method of claim 11, further comprising visually representing at least a portion of the endotracheal tube and the detected vocal cords(s) on a display.

17. The method of claim 11, wherein the endotracheal tube further includes at least one inflatable balloon that extends longitudinally along at least a portion of an outer surface of the endotracheal tube, and wherein the at least one sensor is positioned on or embedded within the at least one elongate balloon, the method further comprising:
aligning the at least one sensor with respect to the detected vocal cord(s);
inflating the at least one elongated balloon such that the at least one sensor moves towards the detected vocal cord(s); and
detecting the detected vocal cord(s) using the at least one sensor while the elongated balloon is inflated.

18. An endotracheal system, comprising:
an elongate tube having a proximal end, a distal end, and a lumen extending therebetween, the elongate tube configured to be positioned in a trachea;
an airway occlusion cuff located closer to the distal end of the elongate tube than the proximal end of the elongate tube; and
a sensor array extending circumferentially around an outer surface of the elongate tube and extending along a length of the elongate tube proximal of the airway occlusion cuff, the sensor array comprising at least one infrared emitter and at least one phototransistor;
the sensor array being configured to detect vocal cord(s) and produce sensor data representing the detected vocal cords(s) when the elongate tube is positioned within the trachea; and
a signal processing unit being configured to receive sensor data and identify the detected vocal cords(s).

19. The endotracheal system of claim 18, wherein the sensor array further comprises a flex circuit extending circumferentially around the outer surface of the elongate tube and an outer case surrounding the flex circuit.

20. The endotracheal system of claim 19, wherein the flex circuit includes a plurality of the infrared emitters and a plurality of the phototransistors placed in a circular array around the flex circuit.

21. An endotracheal system comprising:
an endotracheal tube having a proximal end, a distal end, and a lumen between the proximal end and the distal end, the endotracheal tube configured to be positioned in a trachea;

means supported by the endotracheal tube for detecting vocal cords(s) comprising at least at least one infrared emitter and at least one detector;

means for identifying the vocal cords(s) when the endotracheal tube is positioned within the trachea; and means for determining a distance between the identified vocal cords(s) and a known point on the endotracheal tube.

22. The endotracheal system of claim 21, wherein the means for determining the distance between the identified vocal cords(s) and a known point on the endotracheal tube is further configured to display a visual representation of the distance between the identified vocal cords(s) and the known point on the endotracheal tube.

* * * * *